United States Patent [19]

Schmid et al.

[11] Patent Number: 5,156,050
[45] Date of Patent: Oct. 20, 1992

[54] ULTRASONIC PROBE AND METHOD FOR OPERATING THE SAME

[75] Inventors: Rudi Schmid, Hemhofen; Hans-Jürgen Achtzehn, Adelsdorf, both of Fed. Rep. of Germany

[73] Assignee: Siemens Aktiengesellschaft, Munich, Fed. Rep. of Germany

[21] Appl. No.: 672,693

[22] Filed: Mar. 18, 1991

[51] Int. Cl.⁵ .................. G01N 29/24; G01N 29/10
[52] U.S. Cl. .................................. 73/628; 73/644; 73/629; 73/761
[58] Field of Search .............. 73/620, 624, 625, 626, 73/627, 628, 634, 642, 644, 761, 581, 622; 310/326, 327, 328, 334, 336

[56] References Cited

U.S. PATENT DOCUMENTS

| | | | |
|---|---|---|---|
| 3,546,924 | 12/1970 | Nussbaum et al. | 73/644 |
| 3,685,350 | 8/1972 | Pettinato | 73/641 |
| 3,759,090 | 9/1973 | McFaul et al. | 73/761 |
| 4,014,208 | 3/1977 | Moore et al. | 73/629 |
| 4,864,178 | 9/1989 | Bjurling et al. | 73/644 |

FOREIGN PATENT DOCUMENTS 2209906 9/1973 Fed. Rep. of Germany .
2636107 2/1976 Fed. Rep. of Germany .
2591342 6/1987 France .

Primary Examiner—Hezron E. Williams
Assistant Examiner—Rose M. Finley
Attorney, Agent, or Firm—Herbert L. Lerner; Laurence A. Greenberg

[57] ABSTRACT

An ultrasonic probe for ultrasonically testing screws includes an ultrasonic transducer array having a plurality of ultrasonic transducers. The ultrasonic transducers selectively operate as transmitters and receivers. Coupling bodies of solid material are each acoustically coupled to a respective one of the ultrasonic transducers. Each of the coupling bodies have a free coupling surface facing away from the respective ultrasonic transducer. The coupling surfaces are adapted to the shape of the surface of a head of a screw to be tested. The coupling surfaces are centered on the head of the screw. A method for operating an ultrasonic probe includes placing and centering the coupling surfaces on the surface of the head of the screw. Different ultrasonic transducers are operated in at least one of transmission and reception modes in each of a plurality of measuring steps, for locating and characterizing a flaw in the material of the screw.

17 Claims, 3 Drawing Sheets

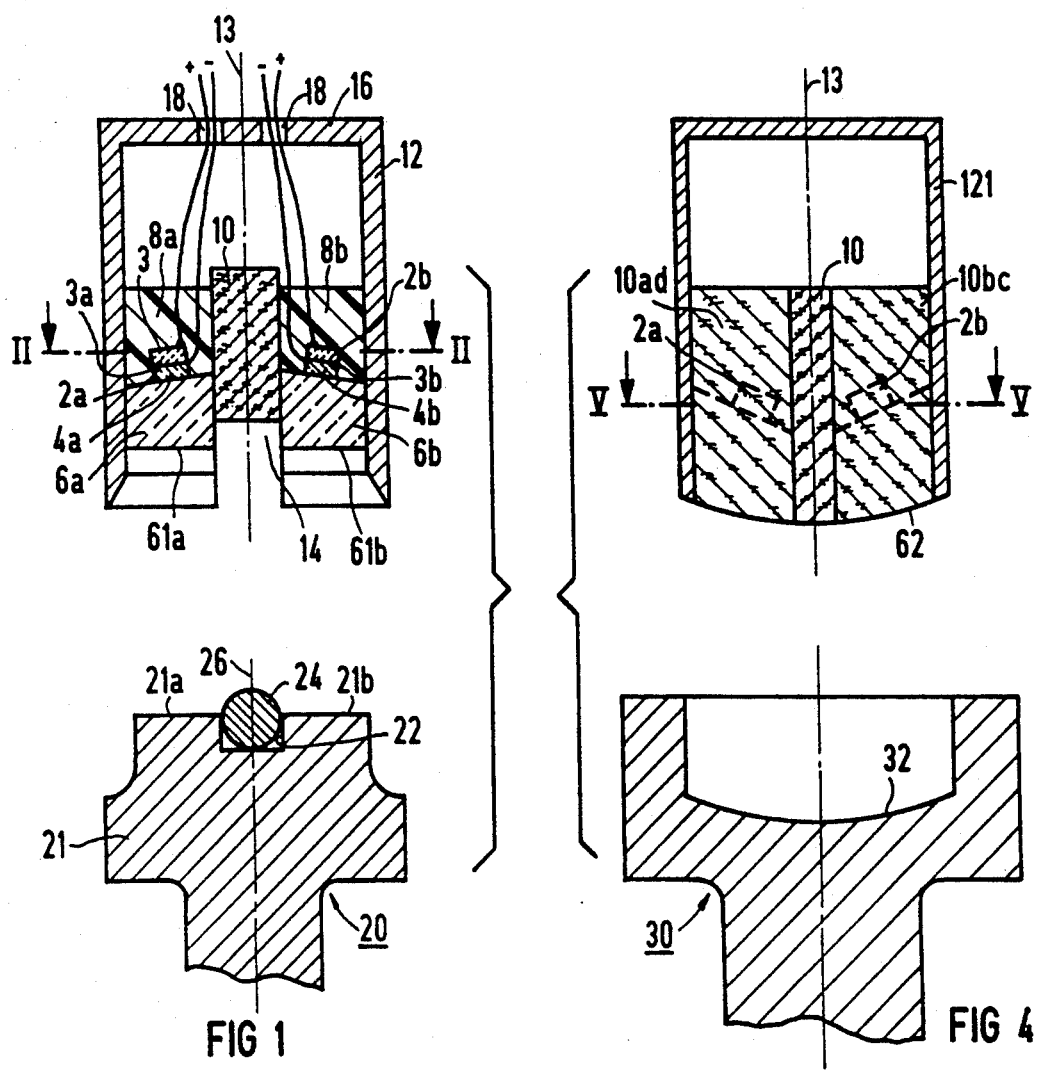
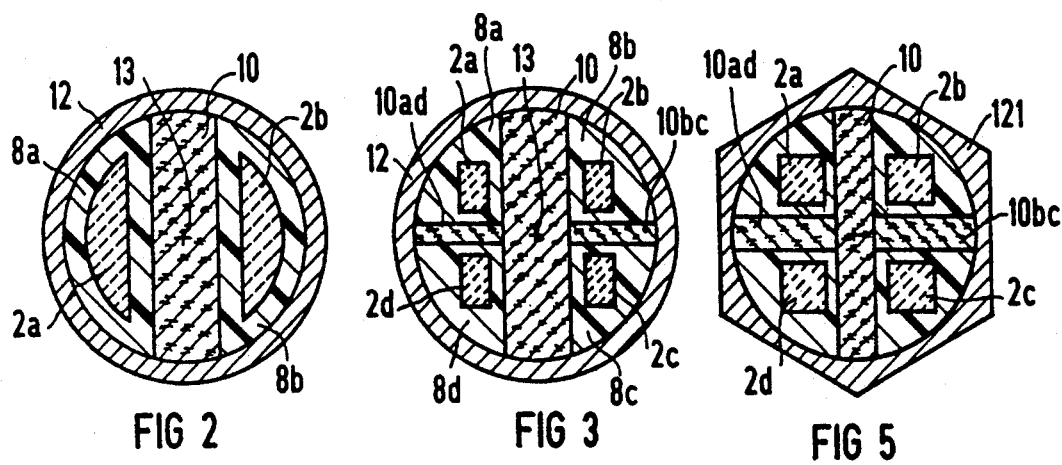
FIG 1 FIG 4
FIG 2 FIG 3 FIG 5

ULTRASONIC PROBE AND METHOD FOR OPERATING THE SAME

The invention relates to an ultrasonic probe for ultrasonically testing screws by the pulse echo method, and a method for operating the probe.

In many cases, checking the strength and reliability of screw connections requires nondestructive testing of the installed screws. This is the case in nuclear facilities, for instance, in which the fastening screws of system parts that are relevant to safety must be checked regularly. Examples thereof are core containment screws, with which the core framework is secured in the core containment in the reactor pressure vessel of a nuclear reactor. Such screws are under water and are particularly threatened by stress corrosion cracking.

In order to test such screws, ultrasonic test methods operating by the pulse echo method are used as a rule. To this end, an ultrasonic probe having an ultrasonic transducer is placed on the head of a screw, and a sonogram is taken. Known probes either contain a single ultrasonic transducer, which is operated as both a transmitter and a receiver, or two ultrasonic transducers, one of which is intended only as a transmitter and the other only as a receiver. The known probes are constructed only for a single testing task, for example the detection of flaws in the form of crack surfaces extending transversely to the axis of the screw and in the vicinity of the screw shank. Flaws in other regions of the screw or flaws having a different orientation relative to the screw axis can then only be inadequately detected with that kind of a probe. Several different probes must therefore be used in order to be sure that all of the flaws can be reliably found. The time expenditure and the attendant radiation exposure to humans in nuclear facilities are correspondingly high.

It is accordingly an object of the invention to provide an ultrasonic probe and a method for operating the same, which overcome the hereinafore-mentioned disadvantages of the heretofore-known methods and devices of this general type and with which the location and structure of the flaw in the screw can be analyzed with the greatest possible accuracy.

With the foregoing and other objects in view there is provided, in accordance with the invention, an ultrasonic probe for ulrasonically testing screws, comprising an ultrasonic transducer array having a plurality of ultrasonic transducers; the ultrasonic transducers selectively operating as transmitters and receivers; coupling bodies of solid material each being acoustically coupled to a respective one of the ultrasonic transducers; each of the coupling bodies having a free coupling surface facing away from the respective ultrasonic transducer, the coupling surfaces being adapted to the shape of the surface of a head of a screw to be tested; and means for centering the probe on the head of the screw.

Since the coupling surfaces are adapted to the shape of the surface of the screw head and because of the means for centering the probe, it becomes possible to provide low-reflection coupling-in of ultrasound to the screw in a manner that is reproducible in terms of measurement conditions.

Since the ultrasonic probe is provided with an ultrasonic transducer array having a plurality of ultrasonic transducers that can be operated as both transmitters and receivers, different test tasks can also be performed without having to change the ultrasonic probe. In an ultrasonic probe according to the invention having two ultrasonic transducers, a great number of operating modes become possible. Depending on the symmetry of the construction, more than one of these modes can be acoustically equivalent, or in other words equivalent in terms of the desired measurement findings from the echo image. For instance, the two modes in which one ultrasonic transducer is operated as a transmitter and the other as a receiver, are acoustically equivalent. Two other modes result if one of the ultrasonic transducers is active as both a transmitter and as a receiver, while the other ultrasonic transducer is not activated. Still other modes are conceivable that can be attained from the rules of combinatorial analysis, by distributing four operating states (transmitter; receiver; transmitter and receiver; and unactivated, respectively) among two ultrasonic transducers. In the case of an ultrasonic probe having two ultrasonic transducers, the result then is three modes that are preferred from the standpoint of measurement technology. They differ from one another markedly in terms of the testing tasks that can be performed with them. For instance, the first mode mentioned, in which one ultrasonic transducer is operated as a transmitter and the other as a receiver, is primarily suited for detecting flaws in the shank of the screw and in the vicinity of the bottom of the screw, while the other two modes, in which only one ultrasonic transducer is activated at a time, are primarily suited for flaws in the transitional region between the head and the shank of the screw.

In accordance with another feature of the invention, the ultrasonic transducers are each separated from one another by an acoustic separating layer, to suppress direct crosstalk.

The coupling bodies are preferably formed of plastic, in particular polymethyl methacrylate (PMMA), having the free coupling surface thereof facing away from the ultrasonic transducer being adapted to the shape of the surface of the head of the screw.

In accordance with a further feature of the invention, the ultrasonic transducers are disposed in a housing having an axis of symmetry and being provided with means in the vicinity of its opening for centering the ultrasonic probe on the head of the screw.

In accordance with an added feature of the invention, in an ultrasonic probe for testing slotted screws, a housing is provided that can be mounted on the head of the screw and that includes guide means in the vicinity of its opening that enable it to be mounted only in predetermined positions relative to the slot.

In accordance with an additional feature of the invention, particularly for slotted screws that are secured with a securing pin placed in the slot, the housing of the ultrasonic probe is provided with mutually opposed recesses in the vicinity of the opening.

In accordance with yet another feature of the invention, the ultrasonic transducers are mirror-symmetrical relative to a plane of symmetry containing the axis of symmetry, and the axis of symmetry is defined by the guide means in such a manner that after the probe is mounted on the head, the axis of symmetry coincides at least approximately with the central plane of the slot.

In accordance with yet a further feature of the invention, there are provided acoustical separating layers in the plane of symmetry extending from one recess to the opposite recess, with the width of the layers substantially corresponding to the width of the slot.

In accordance with yet an added feature of the invention, the ultrasonic transducers are embedded in damping bodies.

In accordance with yet an additional feature of the invention, in order to increase the intensity of acoustic irradiation into the test specimen, the ultrasonic transducers are provided with an adaptation layer, having an acoustical impedance which corresponds to the geometric mean of acoustical impedance of the coupling body and the acoustical impedance of the ultrasonic transducer.

In accordance with again another feature of the invention, the adaptation layer is λ/4 thick.

In accordance with again a further feature of the invention, there are provided four ultrasonic transducers disposed in mirror symmetry with the planes defined by the separating layers. With this kind of probe, the flaws occurring in a screw can be located and characterized reliably at reasonable testing expense.

With the objects of the invention in view there is also provided a method for operating an ultrasonic probe including an ultrasonic transducer array having a plurality of ultrasonic transducers selectively operating in both transmission and reception modes, coupling bodies of solid material each being associated with a respective one of the ultrasonic transducers, and each of the coupling bodies having a free coupling surface facing away from the respective ultrasonic transducer and being adapted to a shape of a surface of a head of a screw, which comprises placing and centering the probe on the surface of the head of the screw; and operating different ultrasonic transducers in the transmission and/or reception mode in each of a plurality of measuring steps, for locating and characterizing a flaw in the material of the screw.

Different aspects of testing can be focused on, depending on the operating mode of the ultrasonic probe. These focal testing points relate to different types and locations of flaws.

When flaws are present in the head of the screw, in accordance with another mode of the invention, there is provided a method which comprises operating only one of the transducers of the ultrasonic testing head as a transmitter and receiver at a time.

In order to be able to characterize flaws in the transitional region between the head and the shank of the screw, in accordance with a further mode of the invention, there is provided a method which comprises operating one ultrasonic transducer as a transmitter and operating another ultrasonic transducer as a receiver.

In order to detect flaws in the threaded portion or in the vicinity of the bottom of the screw, in accordance with a concomitant mode of the invention, there is provided a method which comprises operating two ultrasonic transducers at a time as transmitters and operating the other two ultrasonic transducers as receivers.

Other features which are considered as characteristic for the invention are set forth in the appended claims.

Although the invention is illustrated and described herein as embodied in an ultrasonic probe and a method for operating the same, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 1 is a fragmentary, diagrammatic longitudinal-sectional view of an ultrasonic probe according to the invention, along with a screw to be tested;

FIG. 2 is a cross-sectional view of an ultrasonic probe taken along the line II—II of FIG. 1, in the direction of the arrows;

FIG. 3 is a view similar to FIG. 2 of another embodiment of the ultrasonic probe;

FIG. 4 is a fragmentary, longitudinal-sectional view of an ultrasonic probe having a coupling surface which is adapted to the surface of a round-bottomed screw to be tested;

Figure 8:
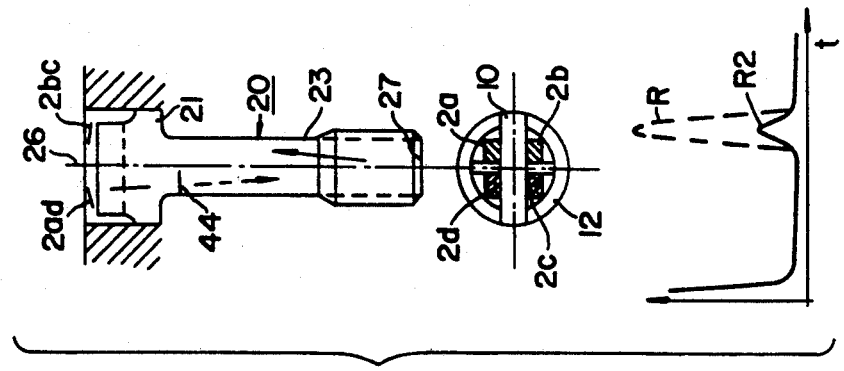

FIG. 5 is a cross-sectional view of the ultrasonic probe taken along the line V—V of FIG. 4, in the direction of the arrows; and FIGS. 6-10 each include a longitudinal-sectional view, a cross-sectional view and a graph of an associated echogram of a preferred ultrasonic probe according to the invention for illustrating various types of flaws in a slotted screw and operating methods, which are particularly well adapted thereto.

Referring now to the figures of the drawing in detail and first, particularly, to FIG. 1 thereof, there is seen an ultrasonic probe including at least two ultrasonic transducers 2a and 2b. The ultrasonic transducers are formed of a piezoelectric material, such as a piezoelectric quartz, and preferably of a piezoelectric ceramic. The ultrasonic transducers 2a and 2b are provided with non-illustrated electrodes, to which electric supply leads are bonded. The ultrasonic transducers 2a and 2b have radiating surface 3a and 3b, each of which is provided with a respective adaptation layer 4a and 4b. The acoustical impedance of these adaptation layers 4a and 4b is preferably approximately equivalent to the geometric mean value for the acoustical impedance of the piezoelectric oscillator material and the acoustical impedance of coupling bodies 6a and 6b. The adaptation layers are preferably approximately λ/4 thick. The coupling bodies 6a and 6b are formed of a solid medium, preferably plastic, and in particular polymethyl methacrylate (PMMA). In order to couple the bodies 6a and 6b of PMMA to the ultrasonic transducers 2a and 2b of a piezoelectric ceramic oscillator material, a glasslike material is particularly well suited for the adaptation layers 4a, 4b.

The coupling bodies 6a and 6b are separated from one another by a separating layer 10 made of a material that is impermeable to sound, such as cork. Direct acoustical crosstalk between the two ultrasonic transducers 2a and 2b is suppressed by this separating layer 10.

The surfaces of the coupling bodies 6a and 6b facing away from the respective ultrasonic transducers 2a and 2b serve as coupling surfaces 61a and 61b, which are adapted to the shape of the surface of the head of a screw to be tested. In the example shown in the drawing, the screw is a slotted screw 20 having flat surfaces 21a and 21b of a cylindrical head 21.

The ultrasonic transducers 2a and 2b are embedded in respective damping bodies 8a and 8b. The damping bodies 8a and 8b are preferably formed of a mixture of epoxy resin, titanium oxide $TiO_2$ and powdered rubber.

In the preferred embodiment shown in the drawing, the ultrasonic probe has a cylindrical housing 12, one end surface of which is closed with a lid 16 that has bores 18 formed therein for electric supply leads for the ultrasonic transducers 2a and 2b. The opposite end surface of the cylindrical housing is open. In the vicinity of the open end surface, the housing 12 protrudes outward past the coupling surfaces 61a and 61b, so that when the ultrasonic probe is mounted on the cylindrical head 21 of the slotted screw 20, it is automatically centered, and an axis 26 of the screw coincides with an axis of symmetry of the ultrasonic probe that penetrates the opening. The shape of the housing 12 incorporating centering means preferably corresponds to the shape of the head of the screw 20 to be tested. In the case of a screw 20 having a cylindrical head shape, the housing 12 preferably has a hollow-cylindrical shape in the vicinity of its opening. However, centering may instead be attained by some other housing shape, such as a regular polygon.

In the example shown in the drawing, a slotted screw 20 is provided, in which a securing pin 24 that protrudes beyond the end surface of the head 21 of the screw is placed in a slot 22 formed in the head 21. In the vicinity of the opening, the housing 12 of the ultrasonic probe is provided with guide means in the form of two recesses 14, which are in alignment with the separating layer 10. As a result of these recesses 14, the separating layer 10 is always aligned parallel to the securing pin 24 when the ultrasonic probe is mounted on the slotted screw.

The ultrasonic transducers 2a and 2b are disposed in mirror symmetry with a plane of symmetry that extends parallel to the separating layer 10 and contains an axis of symmetry 13 of the housing 12. The acoustic irradiation into the slotted screw 20 then takes place in a defined manner, and is aimed at the two circular-segmental surfaces of the head 21 of the screw, which are separated by the slot 22 and the securing pin 24.

The separating layer 10 is preferably at least as wide as the slot 22 and is set back relative to the coupling surfaces 61a and 61b of the coupling bodies 6a and 6b, for receiving the securing pin 24.

Normals to the irradiating surfaces 3a and 3b of the ultrasonic transducers 2a and 2b, in the example shown in the drawing, are inclined relative to the axis of symmetry 13 and to the normals to the surfaces of the coupling surfaces 61a and 61b. The surfaces of the coupling bodies 6a and 6b facing toward the respective ultrasonic transducers 2a and 2b are likewise correspondingly inclined relative to the coupling surfaces 61a and 61b. This angle of inclination is approximately 4° to 8°, for example, and depends both on the task of testing and on the geometrical shape of the screw. In the case of a screw as shown in the exemplary embodiment of the drawing, the ultrasonic transducers 2a and 2b are preferably inclined relative to the axis of symmetry 13 in such a way that the sound emitted is propagated in the direction toward the axis of symmetry 13.

FIG. 2 shows a preferred embodiment in which ultrasonic transducers 2a and 2b that have a circular-segmental cross-sectional area are provided. This assures particularly good adaptation to the likewise circular-segmental surfaces of the head of a slotted screw.

In the particularly preferred embodiment of FIG. 3, four ultrasonic transducers 2a–d are provided, each of which is embedded in a respective damping body 8a, 8b, 8c and 8d and decoupled acoustically from one another by separating layers 10, 10bc and 10ad. The central planes of these separating layers 10, 10ad, 10bc intersect one another in a straight line that coincides with the axis of symmetry 13. Preferably, as shown in the drawing, the ultrasonic transducers 2a–d are disposed in mirror symmetry with these planes formed by the separating layers. An ultrasonic probe having these characteristics in terms of shape is particularly well suited to detect flaws that are located in an arbitrary peripheral position in the head of the screw and at the transition between the head and the shank of the screw.

In the exemplary embodiment of FIG. 4, an ultrasonic probe for a socket screw 30, for instance a hexagonal socket screw with a spherical socket bottom 32, is provided with a a housing 121 and a coupling surface 62 that likewise has the shape of a spherical surface. The coupling surface 62 is formed by non-illustrated surfaces of the coupling bodies that are associated with the respective ultrasonic transducers 2a and 2b. In order to ensure a form-locking mounting of the ultrasonic probe on the spherical socket bottom 32 without voids, the end surfaces of the separating layers 10, 10bc and 10ad are also adapted to the shape of the surface of the socket screw 30 in the vicinity of the opening. The ultrasonic transducers 2a and 2b are preferably inclined outwardly, so that when the probe is mounted on the socket screw 30, emission of sound is effected in the direction of the outer surface of the shank of the screw. Flaws in the transitional region between the head and the shank and in the vicinity of the outer surface of the shank can thus be better detected. The inclination is preferably selected in such a way that the normal to the surface originating at the middle of the ultrasonic transducer 2a or 2b penetrates the coupling surface 62 approximately perpendicularly.

In FIG. 5, the side wall of the housing 121 is adapted to the shape of the head of the screw, so that when the probe is mounted on the spherical socket bottom, centering automatically takes place. Four ultrasonic transducers 2a–d are preferably provided and separated from one another by the acoustical separating layers 10, 10bc and 10ad.

Figure 6:
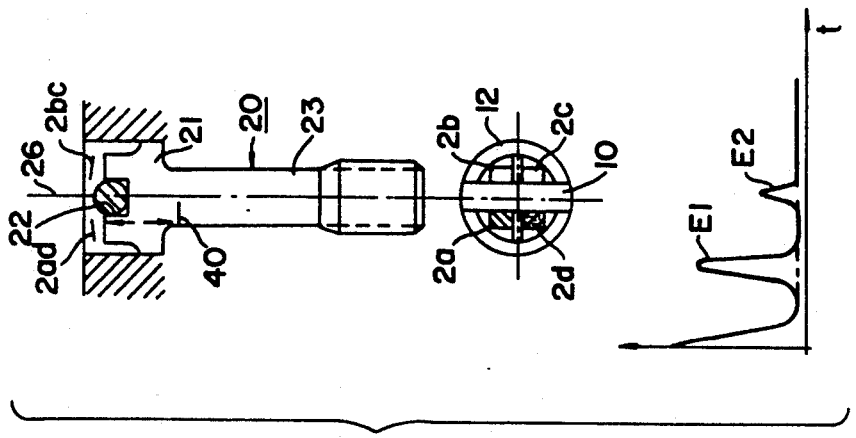

FIG. 6 shows a slotted screw 20 having a flaw 40 in the transitional region between the head 21 and a shank 23 of the screw. The flaw 40 is a crack surface which begins at the edge of the slotted screw 20, is oriented perpendicularly to the axis 26 of the screw and has a circular-segmental shape, the chord of which extends parallel to the slot 22 in the screw. The probe mounted on the slotted screw 20 is diagrammatically indicated by the oblique dashed lines marked by reference numerals 2ad and 2bc. The associated operating mode is illustrated in terms of a diagrammatic cross section shown below the screw. In this operating mode, the ultrasonic transducer 2a shown with shading from the upper right to the lower left serves as a receiver, while the ultrasonic transducer 2d shown with shading from the upper left to the lower right serves as a transmitter. The two ultrasonic transducers 2c and 2b are not activated in this mode. The ultrasonic waves originating at the ultrasonic transducer 2d and the ultrasonic waves received by the ultrasonic transducer 2a are represented in the drawing by arrows. An associated echogram, in which the signals received by the ultrasonic transducer 2a are plotted over time, includes two echo signals E1 and E2, which are respectively produced as the result of single and double reflection at the flaw 40. The broken line shown in the echogram of FIG. 6 is equivalent to the echogram of a flawless screw.

Figure 7:
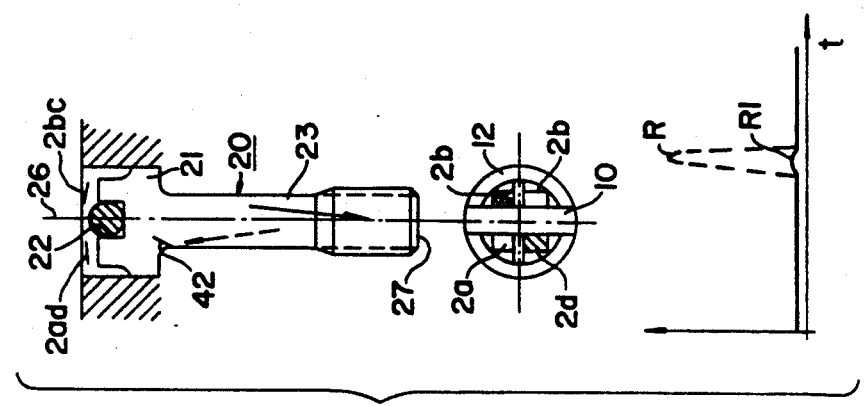

In FIG. 7, a likewise substantially two-dimensional flaw 42 is shown in the transitional region between the head 21 and the shank 23 of the screw. The flaw 42 is oriented at an inclination relative to the axis 26 of the screw. Such a flaw is only detectable with difficulty if measurement in the operating mode of FIG. 6 is used. In FIG. 7, an operating mode is therefore provided in which two ultrasonic transducers 2b and 2d which are diagonally opposed to one another, are respectively provided as the transmitter and receiver. The ultrasound coupled into the screw from the ultrasonic transducer 2b reaches a screw bottom 27 unhindered, is reflected there and is shaded by the flaw 42, so that it cannot be received by the ultrasonic transducer 2d. In the echogram of FIG. 7, it can be seen that for a flawless screw, an echo signal R shown in broken lines is received by the ultrasonic transducer 2d. If a flaw 42 is present, then instead of the echo signal R, only a markedly reduced echo signal R1 occurs.

In the example of FIG. 8, a substantially two-dimensional, circular-segmental flaw 44 is shown in the vicinity of the transition between the head 21 and the shank 23 of the screw. The flaw is oriented transversely to the axis 26 of the screw, and its chord extends perpendicularly to the screw slot 22. In order to detect this kind of flaw, it is suitable to use two ultrasonic transducers 2c and 2d that are opposite one another with respect to the separating layer 10, as the transmitters, and to use the remaining two ultrasonic transducers 2a and 2b as the receivers. It can be seen from the echogram of FIG. 8 that in this case as well, the echo signal R produced by a flawless screw is suppressed by shading of the ultrasound emitted by the ultrasonic transducers 2c and 2d, so that an echo signal R2 reflected from the screw bottom 27 is markedly reduced.

Figure 9:
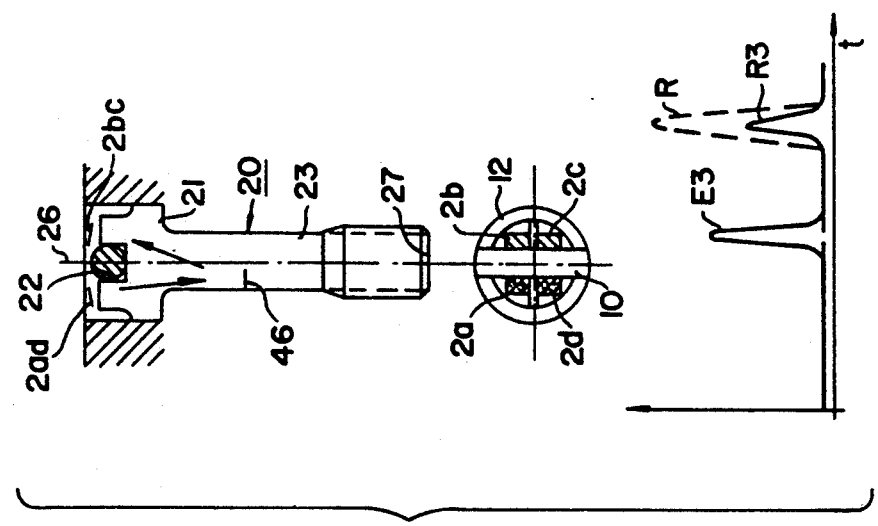

FIG. 9 shows a slotted screw with a flaw 46 having a circular-segmental crack surface oriented perpendicularly to the axis 26 of the screw and located in the middle of the screw shank 23. The chord of this crack location extends parallel to the screw slot 22. In order to detect this kind of flaw 46, it is advantageous to use two ultrasonic transducers 2a and 2d at a time as transmitters and two ultrasonic transducers 2b and 2c at a time as receivers. The ultrasonic transducers 2a and 2d that operate as transmitters and the ultrasonic transducers 2b and 2c used as receivers are separated from one another by the separating layer 10 extending parallel to the screw slot 22. The corresponding echogram shown in FIG. 9 has an echo pulse signal E3, which is produced at the flaw 46. An echo signal R3 that is reflected from the screw bottom 27 also occurs, but as compared with the echo signal R that is measured in a flawless screw, the signal R3 is markedly reduced.

Figure 10:
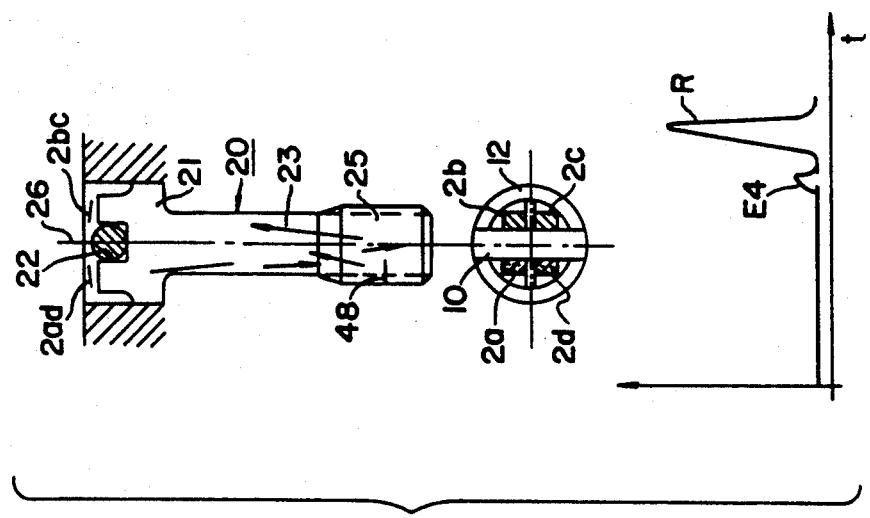

FIG. 10 shows a flaw 48 which is of the same type as in FIG. 9 but is located in a threaded part 25 of the screw 20. The preferred operating mode of the ultrasonic probe corresponds to the mode of the example of FIG. 9. Before the occurrence of the echo signal R reflected from the screw bottom 27, an echo signal E4 also occurs, which cannot be observed in a flawless screw.

The types of operating modes of the ultrasonic probe according to the invention shown in FIGS. 6–10 are not a complete selection of operating possibilities. Instead, these examples are merely intended to illustrate the fact that the great number of possible types of operation enable reliable determination and characterization of most types of flaws occurring in a screw.

We claim:

1. An ultrasonic probe for ulrasonically testing screws, comprising:
   a) an ultrasonic transducer array having a plurality of ultrasonic transducers whereby said ultrasonic transducers are selectively operated as transmitters and receivers;
   b) coupling bodies of solid material each being acoustically coupled to a respective one of said ultrasonic transducers;
   c) each of said coupling bodies having a free coupling surface facing away from said respective ultrasonic transducer, said coupling surfaces shaped to accommodate the surface of a head of a screw to be tested; and
   d) means for centering said coupling surfaces on the head of the screw.

2. The ultrasonic probe according to claim 1, including an acoustical separating layer separating said ultrasonic transducers from one another to suppress direct crosstalk.

3. The ultrasonic probe according to claim 1, including a housing in which said ultrasonic transducers are disposed, said housing having an opening formed therein for the exit and entry of sound and an axis of symmetry passing through said opening, and said housing having said centering means in the vicinity of said opening.

4. The ultrasonic probe according to claim 3, wherein said housing has guide means in the vicinity of said opening for enabling said housing to be mounted on the head of the screw only in predetermined positions relative to a slot in a slotted screw to be ultrasonically tested.

5. The ultrasonic probe according to claim 4, wherein said guide means are in the form of mutually opposite recesses formed in said housing in the vicinity of said opening, for ultrasonically testing slotted screws having a securing pin placed in the slot.

6. The ultrasonic probe according to claim 4, wherein said ultrasonic transducers in said array are mirror-symmetrical to a plane of symmetry containing the axis of symmetry of said housing, said plane of symmetry being defined by said guide means and at least approximately coinciding with a central plane of the slot of the slotted screw after the probe has been mounted on the head of the screw.

7. The ultrasonic probe according to claim 6, wherein said guide means are in the form of two mutually opposite recesses formed in said housing in the vicinity of said opening, for ultrasonically testing slotted screws having a securing pin placed in the slot, and including an acoustical separating layer extending in said plane of symmetry and having a width substantially corresponding to the width of the slot in the slotted screw.

8. The ultrasonic probe according to claim 1, wherein said array has four ultrasonic transducers.

9. The ultrasonic probe according to claim 3, wherein said ultrasonic transducers have radiating surfaces being inclined relative to the axis of symmetry of said housing.

10. The ultrasonic probe according to claim 1, including damping bodies in which said ultrasonic transducers are respectively embedded.

11. The ultrasonic probe according to claim 9, wherein said ultrasonic transducers have adaptation layers respectively disposed on said radiating surfaces.

12. The ultrasonic probe according to claim 11, wherein said adaptation layers are $\lambda/4$-thick.

13. A method for operating an ultrasonic probe, the ultrasonic probe including an ultrasonic transducer array having a plurality of ultrasonic transducers selectively operating in transmission and reception modes, coupling bodies of solid material each being associated with a respective one of the ultrasonic transducers, and each of the coupling bodies having a free coupling surface facing away from the respective ultrasonic transducer and being adapted to a shape of a surface of a head of a screw, and the method which comprises:
  a) placing and centering the coupling surfaces on the surface of the head of the screw; and
  b) operating different ultrasonic transducers in at least one of the transmission and reception modes in each of a plurality of measuring steps, for locating and characterizing a flaw in the material of the screw.

14. The method according to claim 13, which comprises operating only one of the ultrasonic transducers in the transmission and reception modes in the measuring steps.

15. The ultrasonic probe according to claim 13, which comprises operating one of the ultrasonic transducers in the transmission mode and operating another of the ultrasonic transducers in the reception mode in the measuring steps.

16. The ultrasonic probe according to claim 13, which comprises placing at least four ultrasonic transducers in the array, and operating two ultrasonic transducers at a time in the transmission mode and another two ultrasonic transducers at a time in the reception mode in the measuring steps.

17. A method for operating an ultrasonic probe, which comprises:
  a) placing solid coupling bodies on respective ultrasonic transducers of a transducer array with free coupling surfaces of the coupling bodies facing away from the respective ultrasonic transducers and being shaped to accommodate the shape of a surface of a head of a screw;
  b) placing and centering the coupling surfaces on the surface of the head of the screw; and
  c) operating different ultrasonic transducers in at least one of transmission and reception modes in each of a plurality of measuring steps, for locating and characterizing a flaw in the material of the screw.

* * * * *